United States Patent [19]
Gorissen et al.

[11] Patent Number: 5,424,076
[45] Date of Patent: Jun. 13, 1995

[54] METHOD OF PRODUCING MICROSCOPIC PARTICLES MADE OF HYDROLYTICALLY DECOMPOSABLE POLYMERS AND CONTAINING ACTIVE SUBSTANCES

[75] Inventors: Elke Gorissen, Offenburg; Heike Biskup, Langenfeld; Hannelore Schneider, Dusseldorf, all of Germany

[73] Assignee: Schwarz Pharma AG, Monheim, Germany

[21] Appl. No.: 81,272

[22] PCT Filed: Dec. 18, 1991

[86] PCT No.: PCT/DE91/01002
§ 371 Date: Jun. 22, 1993
§ 102(e) Date: Jun. 22, 1993

[87] PCT Pub. No.: WO92/11000
PCT Pub. Date: Jul. 9, 1992

[30] Foreign Application Priority Data
Dec. 22, 1990 [DE] Germany .............. 40 41 563.5

[51] Int. Cl.[6] .................. A61K 9/50; A61K 9/14; B01J 13/02; B32B 5/16
[52] U.S. Cl. ........................ 424/501; 424/451; 424/452; 424/455; 424/462; 424/489; 514/963; 264/4.6; 428/402.21; 428/402.22

[58] Field of Search ............... 424/489, 501, 451, 452, 424/455, 462; 264/4.6; 514/963; 428/402.21, 402.22

[56] References Cited
U.S. PATENT DOCUMENTS
5,232,707  8/1993  Lokensgard ............... 424/490
5,271,945  12/1993  Yoshioka et al. ........... 424/489

FOREIGN PATENT DOCUMENTS
0275961  7/1988  European Pat. Off. .
0315875  5/1989  European Pat. Off. .
0322687  7/1989  European Pat. Off. .
0350246  1/1990  European Pat. Off. .
0421577A2  4/1991  European Pat. Off. .
666407  7/1988  Switzerland .
91/09079  7/1989  WIPO .

*Primary Examiner*—Thurman K. Page
*Assistant Examiner*—Carlos Azpuru
*Attorney, Agent, or Firm*—Marshall, O'Toole, Gerstein, Murray & Borun

[57] ABSTRACT

The invention concerns a method for the production of microscopic particles made of hydrolytically decomposable polymers, in particular copolymers, and containing active substances, using fluid gas with a uniform particle-size distribution and by the addition of biologically compatible amino acids. The microscopic particles produced by this method can be used as drugs for the treatment of humans or animals.

8 Claims, 1 Drawing Sheet

METHOD OF PRODUCING MICROSCOPIC PARTICLES MADE OF HYDROLYTICALLY DECOMPOSABLE POLYMERS AND CONTAINING ACTIVE SUBSTANCES

This invention relates to a method for manufacturing microparticles containing active substances from hydrolyrically decomposable polymers.

It has been known from numerous publications that resorbable polyesters, in particular those with a lactic acid base or glycolic acid base, and especially their copolymers, are completely decomposed into endogenous compounds in human or animal tissue or in human or animal fluids, wherein, depending on the purpose of use, the decomposition rates of the polymers can be varied from a few hours up to several months.

The decomposition products reach the normal biochemical metabolism and are either directly excreted or finally metabolized into water and carbon dioxide.

Of particular interest and importance are the applications of resorbent polyesters in galenic preparations with delayed release of active substances for the manufacture of stock forms.

However, these kinds of polyesters can only then be used in human or animal organisms, if they are free of impurities, which possibly may cause irritations. These impurities are, for example, nonconverted residual monomers, molecular weight regulators, or polymerization catalysts.

The present state of the art is represented in

Sustained release (drug) formulations, which are manufactured by using these types of resorbent polyesters that are suitable for subcutaneous injections or implantations into the body, have been manufactured up to now according to the following processes:

microencapsulation with organic solvents (L. M. Sanders et al., *J. Contr. Release*, 2 (1985) 187, or P. B. Deasy, *Microencapsulation and Related Drug Processes*, M. Dekker Inc., New York 1984);

emulsification and subsequent solvent evaporation, T. R. Tice & R. M. Gilley, *J. Contr. Release*, 2 (1985) 343);

spray drying (D. L. Wise et al., *Life Sci.*, 19 (1976) 867;

extrusion (A. J. Schwope et al., *Life Sci.*, 17 (1975) 1877);

fusion embedding (A. J. Schwope et al., *Life Sci.*, 17 (1975) 1877); or boundary surface polymerization (G. Birrenbach & P. Speiser, *J. Pharm. Sci.*, 65 (1976) 1763).

The above-mentioned processes either have the disadvantage of requiring large amounts of toxic organic solvents, wherein the resulting sustained releae (drug) formulations have high solvent residual concentrations in the form of polymer embeddings (see, J. P. Benoit et al., *Int. J. Pharmaceutics*, 29 (1986) 95); or, the mentioned processes require high temperatures or pressures, which, in particular, lead to high localized temperature increases and can damage the incorporated medicaments (see L. M. Sanders et al., *J. Pharm. Sci.*, 75 (1986) 356). If such a medicament type remains under the skin or in the tissue over an extended period of time, toxic tissue reactions can be expected locally from the organic solvents. Therefore, the solvent residues must be removed as thoroughly as possible from the mentioned products.

A detailed description of the above-mentioned manufacturing process of the present state of the art is found in DE-OS 37 44 329.

Finally, a process described as "Aerosol Solvent Extraction System" (ASES) for the manufacture of drug-containing microparticles loaded with active substance is known from EP P 322 687 A2. In this process, active substance-loaded microparticles are manufactured with the aid of fluid gases. Microparticles are formed in a supercritical atmosphere from a solution of polymers and active substance, wherein the solvent is removed by absorption into the gas phase.

Although this method is suitable for manufacturing auto-sterile active drug-containing microparticles with a minimum of organic solvents (below 10 ppm) without residual monomers, molecular weight regulators, or polymerization catalyzers, it is, however, disadvantageous in that, with larger batches, no reliable constant particle size distribution can be achieved and in that not all hydrolytically decomposable polymers can be reliably processed into microparticles.

Therefore, it is the object of this invention to manufacture active substance-containing microparticles with constant particle size distribution from hydrolyrically decomposable polymers, in particular, from copolymers of lactic acid and glycolic acid.

This object is achieved in accordance with the present invention in that, each time at least one physiologically compatible amino acid of a solution of hydrolytically decomposable polymers or copolymers and of at least one active substance in the corresponding solvents is added, microparticles are formed in a supercritical atmosphere, wherein the solvents are removed by absorption in the gas phase.

In accordance with this invention, any active substance can be used. Examples of the active substances are medicaments, toxins, and viruses. We refer to U.S. Pat. No. 3,773,919 with respect to this concept.

All biologically compatible, hydrolyrically decomposable polymers and copolymers can be used as carrier substances.

We would like to name the following:

Poly-1-lactide (1-PLA), poly-d,1-lactide (PLA), poly-1-lactide-coglycolides (1-PLGA), as well as poly-d,1-lactide-coglycolides (PLGA) with variable portions of the monomers of lactic acid (PLA) and glycolic acid (GA). Preferably, the polymer lactide-coglycolide comprises a molar ratio between 85:15 and 50:50. In particular, the molar ratio 75:25 is preferred.

Amino acids which can be used in the invention, without restriction include L-lysine, L-phenylalanine, L-tryptophane, and D,L-phenylalanine.

According to an embodiment of this invention, nitrous oxide, carbon dioxide, halogenated hydrocarbons, saturated or unsaturated hydrocarbons, dinitrogen dioxide ($N_2O_2$), or ammonia, or mixtures thereof, can be used as fluid gases.

The invention will be better understood from the following description thereof, taken in conjunction with accompanying FIG. 1, which shows a flow diagram of a process suitable for making the compositions of the invention.

According to another embodiment of the invention, correspondingly suited gases, as well as the low-boiling liquids and mixtures thereof, which are convertible into a supercritical condition, can each be used as a fluid gas.

DESCRIPTION OF THE PREFERRED EMBODIMENTS

Figure 1:
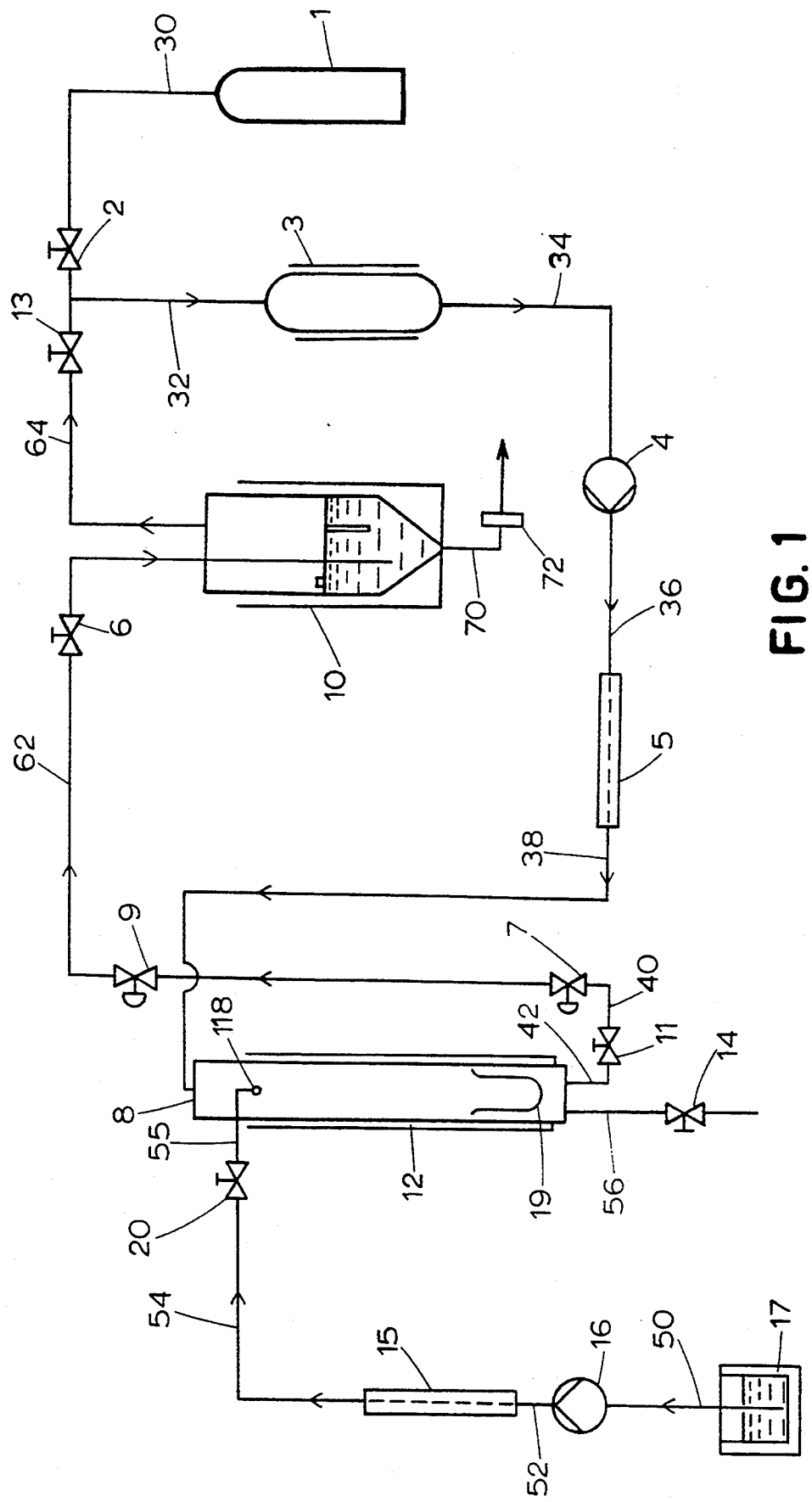

The following examples illustrate the invention.

EXAMPLE 1

Manufacture of Microparticles Containing Buserelin Polymer: poly-(D,L) lactide coglycolide, i.v. 0.8 dl/g 0.375 g L-lysine (Aldrich) is dissolved in 25 ml glacial acetic acid (Merck); 2.5 g poly-(D,L)lactide coglycolide (monomer ratio 75:25) is dissolved in 75 ml dichloromethane (Merck), Both solutions are united, Then, 0.06 g buserelin is added and stirred, until a clear solution is obtained: 0.06% solution, with reference to buserelin.

This solution is placed in a reservoir 17 (FIG. 1), and fed to a piston stroke pump 16 though line 50. From pump 16, the solution passes through line 52, heat exchanger 15, line 54, valve 20, and line 55, to nozzle 118. At an excess pressure of 94–96 bar, the solution containing buserelin and the copolymer is atomized through a conventional monocomponent nozzle 118, type Schlick 121 V, in tower 12, wherein the $CO_2$, in supercritical condition, at 90 bar/36° C. and a flow rate of 8.9 kg/h, is fed in a parallel flow, via inlet 8, through the tower. Nozzle 118 has a diameter of 0.5 mm, and the spray angle is 10°.

In accordance with the high affinity of the supercritical $CO_2$ for the solvent, solvent is withdrawn from the primarily formed droplets; spherical solid solutions remain. The $CO_2$ loaded with the solvent leaves the tower end through lines 42 and 40 controlled by two magnet valves 7 and 9 and is relieved to 60 bar. The valves are operated to permit the amount of the fluid gas entering the tower per unit time to escape while maintaining the operating pressure of the tower.

The $CO_2$, loaded with solvent which is at a pressure of 60 bar due to the pressure relief, is fed through line 62 to separator 10, which has been heated to 21° C., wherein the solvent mixture separates as a consequence of the severely reduced solubility in the $CO_2$ under these conditions. The $CO_2$, which has been freed from the solvent mixture, is again heated and pressurized to a supercritical condition (90 bar, 36° C.) through lines 64 and 32, and is fed again, for further drying of the formed particles, to tower 12 through inlet 8, via line 34, pump 4, line 36, heat exchanger 5, and line 38.

Removal of the solvent mixture in separator 10 takes place, after the separation of the separator 10 from the circuit, through valves 6 and 13 and relief to atmospheric pressure.

After the completion of the actual spraying, which amounts to about 20 to 50 minutes, the $CO_2$ is fed through the tower until no solvent can be reclaimed any longer in separator 10.

After completion of the drying process, the $CO_2$ flow to tower 12 is shut off, the tower is relieved to atmospheric pressure via valves 11 and 14, and the particles are removed at the lower tower end 19.

The dry powder, which is removed from the tower, consists of spheres containing buserelin and having a diameter of 5 to 10 $\mu$m.

EXAMPLE 2

Manufacture of Microparticles Containing LH-RH-Antagonist Polymer: Poly-(D,L) lactide coglycolide, i.V. 0.8 dl/g The manufacture takes place following the method of Example 1.

0.375 g L-lysine (Aldrich), 0.06 g LH-RH-Antagonist, 2.5 g poly(D,L-)lactide coglycolide (75:25) i.V. 0.8 dl/g are dissolved together with 25 ml glacial acetic acid (Merck) and 75 ml dichloromethane (Merck) and stirred until a clear solution is obtained.

This solution is sprayed at 94–96 bar excess pressure in the tower of the high pressure unit. $CO_2$ at 90 bar/36° C. is fed in parallel flow through the tower. The $CO_2$ flow rate amounts to 8.9 kg/h. A conventional mono-component nozzle of the Schlick 121 V type serves as a nozzle, having a nozzle diameter of 0.5 mm and a spray angle of 10°.

After completion of the actual spray time, the $CO_2$ is fed through the tower until no solvent is reclaimed in the separator of the high pressure unit.

The dry powder obtained from the tower consists of spheres with a diameter of 5–10 $\mu$m.

EXAMPLE 3

Manufacture of Microparticles Which Do Not Contain an Active Substance

The manufacture takes place following the method of Example 1.

A solution of 2.5 g poly-(D,L)lactide coglycolide, 75:25 i.V 0.8 dl/g in 75 ml dichloromethane and 25 ml glacial acetic acid (all Merck), which contains 0.375 g L-lysine (Aldrich), is atomized at about 94–96 bar excess pressure in the tower of the high pressure unit. Simultaneously, the $CO_2$ is fed at 90 bar/36° C. in parallel flow through the tower. The $CO_2$ flow rate amounts to 8.9 kg/h. A conventional mono-component nozzle of the Schlick type 121 V with a diameter of 0.5 $\mu$m and a spray angle of 10° serves as a nozzle.

After completion of the actual spray time, the $CO_2$ is fed through the tower until no solvent is reclaimed in the separator of the high pressure unit.

The dry powder obtained from the tower consists of spheres with a diameter of 5–10 $\mu$m.

Table I summarizes further examples of polymers useful for the manufacture of microparticles containing active substances in accordance with the invention.

The manufacture of those microparticles takes place following the procedure of Examples 1 to 3.

The microparticles, which were thus obtained, are sterile and free of residual solvents, polymerization catalyzers, or initiator molecules.

They have a constant particle size distribution of 5 to 10 $\mu$m.

Therefore, they can be used as a sustained-release drug formulation type for subcutaneous injections or implantations in the body.

TABLE 1

| No. | Polymer | Inherent Viscosity dl/g | Molar Ratio Lactide:Glycolide | Polymer (g) | Active Substance | | Amino Acid (g) |
|---|---|---|---|---|---|---|---|
| | | | | | (g) | Amino Acid | |
| 1 | Poly-(D,L)-lactide | 0.3 | | 2.0 | 0.06 | L-Lysine | 0.5 |
| 2 | Poly-(D,L)-lactide- | 0.8 | 75:25 | 1.0 | 0.03 | L-Phenyl- | 0.25 |

TABLE 1-continued

| No. | Polymer | Inherent Viscosity dl/g | Molar Ratio Lactide:Glycolide | Polymer (g) | Active Substance (g) | Active Substance Amino Acid | Amino Acid (g) |
| --- | --- | --- | --- | --- | --- | --- | --- |
| 3 | Poly-(D,L)-lactide-coglycolide | 0.8 | 75:25 | 2.0 | 0.06 | D,L-Phenyl-alamine | 0.5 |
| 4 | Poly-(D,L)-lactide-coglycolide | 0.8 | 75:25 | 2.2 | 0.06 | L-Tryptophane | 0.55 |
| 5 | Poly-L-lactide | 0.56 | | 6.0 | 0.18 | L-Lysine | 0.9 |
| 6 | Poly-L-lactide | 1.0 | | 3.0 | 0.10 | L-Lysine | 0.45 |

The polymers are dissolved each time in 75 ml dichloromethane (Merck) and 25 ml glacial acetic acid.
The respective amount of amino acid is added. D,L-phenylalanine is to be predissolved suitable in up to 50 ml of ethanol (Merck).

The foregoing detailed description has been given for clearness of understanding only, and no unnecessary limitations should be understood therefrom, as modifications will be obvious to those skilled in the art.

What is claimed is:

1. A process for the manufacture of sustained-release microparticles containing an active substance comprising the steps of
   (a) preparing a solution of a hydrolyrically decomposable polymer in a solvent;
   (b) dissolving or dispersing at least one active substance and at least one free amino acid in said solution;
   (c) atomizing or spraying the dispersion or solution produced in step (b) while simultaneously adding a fluid gas at supercritical conditions, thereby extracting said solvent from said dispersion or solution into said fluid gas, leaving microparticles containing active substance and polymer;
   (d) separating said fluid gas from said microparticles; and
   (e) recovering said microparticles.

2. A process according to claim 1 wherein said polymer is a copolymer.

3. A process according to claim 1 wherein said polymer is selected from the group consisting of poly-1-lactide, poly-d,l-lactide or poly-1-lactide-coglycolides, and poly-d,l-lactide-coglycolides with variable portions of the respective monomer components.

4. A process according to claim 1 wherein said polymer lactide-coglycolide has a molar ratio between 85:15 and 50:15.

5. A process according to claim 1 wherein said amino acid is L-lysine, L-phenylalanine, or L-tryptophane.

6. A process in accordance with claim 1 wherein said amino acid is D,L-phenylalanine.

7. A process in accordance with claim 1 wherein said fluid gas is selected from the group consisting of dinitrogen oxide, carbon dioxide, halogenated hydrocarbons, saturated or unsaturated hydrocarbons, ammonia, and mixtures thereof.

8. A process according to claim 1 wherein said fluid gas is selected from the group consisting of gases and low boiling liquids, and mixtures thereof, which can exist in a supercritical condition.

* * * * *

UNITED STATES PATENT AND TRADEMARK OFFICE
CERTIFICATE OF CORRECTION

PATENT NO.  :  5,424,076

DATED  :  June 13, 1995

INVENTOR(S)  :  Elke Gorissen et al.

It is certified that error appears in the above-identified patent and that said Letters Patent is hereby corrected as shown below:

Column 1, line 32, after "in" insert --DE-OS 37 08 916--

Column 1, line 55, "releae" should be --release--

Column 2, line 44, "Poly-1-lactide (1-PLA)" should be --Poly-l-lactide (l-PLA)--

Column 2, line 44, "poly-d,1-lactide" should be --poly-d,l-lactide--

Column 2, line 45, "poly-1-lactide-coglycolides (1-PLGA)" should be --poly-l-lactide-coglycolides (l-PLGA)--

Column 2, line 46, "d,1-lactide-coglycolides" should be --d,l-lactide-coglycolides--

Column 3, line 12, "united," should be --united.--

Column 3, line 17, "though" should be --through--

Column 3, line 56, "$CO_2$flow" should be --$CO_2$ flow--

Column 4, line 23, "$CO_2$is" should be --$CO_2$ is"

UNITED STATES PATENT AND TRADEMARK OFFICE
CERTIFICATE OF CORRECTION

PATENT NO. : 5,424,076

DATED : June 13, 1995

INVENTOR(S) : Elke Gorissen et al.

It is certified that error appears in the above-identified patent and that said Letters Patent is hereby corrected as shown below:

Column 4, line 44, "$CO_2$is" should be --$CO_2$ is--

Column 6, lines 18-20, "poly-1-lactide, poly-d,1-lactide or poly-1-lactide-coglycolides, and poly-d,1-lactide-coglycolides" should be --poly-l-lactide, poly-d,l-lactide or poly-l-lactide-coglycolides, and poly-d,l-lactide-coglycolides--

Signed and Sealed this

Tenth Day of October, 1995

Attest:

BRUCE LEHMAN

Attesting Officer

Commissioner of Patents and Trademarks